(12) United States Patent
Chirchin et al.

(10) Patent No.: US 8,324,267 B2
(45) Date of Patent: Dec. 4, 2012

(54) KINASE INHIBITORS AND THE USE THEREOF

(75) Inventors: Vladimir Chirchin, Frankfurt am Main (DE); Giannis Athanassios, Leipzig (DE); Ralph Mazitschek, Boston, MA (US); Jonathan Sleemann, Bruchsal (DE)

(73) Assignee: Forschungzentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 10/483,687

(22) PCT Filed: Jul. 12, 2002

(86) PCT No.: PCT/EP02/07778
§ 371 (c)(1),
(2), (4) Date: Jul. 6, 2004

(87) PCT Pub. No.: WO03/007943
PCT Pub. Date: Jan. 30, 2003

(65) Prior Publication Data
US 2004/0248965 A1   Dec. 9, 2004

(30) Foreign Application Priority Data

Jul. 13, 2001  (DE) .................................. 101 34 196

(51) Int. Cl.
*A61K 31/405* (2006.01)
*C07D 209/00* (2006.01)

(52) U.S. Cl. ...................................... 514/415; 548/469

(58) Field of Classification Search .................. 514/415; 548/469
See application file for complete search history.

(56) References Cited

U.S. PATENT DOCUMENTS 5,626,633 A * 5/1997 Roschger .......................... 8/506
6,133,305 A * 10/2000 Tang et al. ..................... 514/418

FOREIGN PATENT DOCUMENTS

| EP | 0632102 | 1/1995 |
| WO | 9640116 | 12/1996 |
| WO | 9807695 | 2/1998 |
| WO | 9910325 | 3/1999 |

OTHER PUBLICATIONS

Kirkin, et al. "Characterization of indolinones which preferentially inhibit VEGF-C and VEGF-D-induced activation of VEGFR-3 rather than VEGFR-2," Eur. J. Biochem., vol. 268, pp. 5530-5540, especially p. 5537.*
Blum et al: "Substrate Competitive Inhibitorsof IGF-1 Receptor Kinase" Biochemistry BD. 39, No. 51, 2000, pp. 15705-15712.
Database Crossfire Beilstein "Online! Beilstein Institut Zur Förderung Der" XP002215778, Bagard, BD. 4, No. 5, 1909, p. 1038.
Hamada K et al: "VEGF-C Signaling Pathways Through VEGFR-S and VEGFR-3 In" W.B. Saunders Co., BD. 12, No. 96, 2000, pp. 3793-3800, XP002952145.
V. Kirkin et al: Characterization of Indolinones Which Preferentially . . . Eur. J. Biochem., BD. 268, November 2001, pp. 5530-5540.

* cited by examiner

*Primary Examiner* — Susannah Chung
(74) *Attorney, Agent, or Firm* — Lucas & Mercanti, LLP (57) ABSTRACT

The present invention relates to protein kinase inhibitors and to the use thereof for the treatment of diseases induced by pathological signal transduction cascades.

1 Claim, 10 Drawing Sheets

Table 1

| RTK | Disease |
|---|---|
| FGFR | Kraniosynostosis |
| | Skeletal dysplasia |
| | Lethal skeletal dysplasia |
| RET | Familial medullary thyroid carcinoma |
| | Multiple endocrine neoplasia of type 2 |
| MET | Hereditary papillary renal cell carcinoma |
| KIT | Gastrointestinal stromal tumors |
| | Mastocytosis |
| TIE2 | Vascular development defects |

Fig. 10:

Table 2

| Angiogenesis-dependent diseases |
| --- |
| Angiofibromal |
| Arterial venous malformation |
| Arthritis |
| Atherosclerotic plaques |
| Neovascularization associated with keratoplasty |
| Delayed wound healing |
| Diabetic retinopathy |
| Granulation formation after burns |
| Hemangioma |
| Hemophilia joints |
| Hypertrophic scars |
| Neovascular glaucoma |
| Poorly healing fractures |
| Osler-Weber syndrome |
| Psoriasis |
| Progenic granuloma |
| Retrolental fibroplasia |
| Scleroderma |
| Tumor formation and metastases |
| Trachoma |
| Vascular adhesion |
| Von Hippel-Lindau syndrome |

KINASE INHIBITORS AND THE USE THEREOF

The present invention relates to protein kinase inhibitors and to the use thereof for the treatment of diseases induced by pathological signal transduction cascades.

Protein kinases are enzymes belonging to the transferases which catalyze the transfer of phosphate residues from adenosine 5'-triphosphate (ATP) or guanosine 5'-triphosphate (GTP) to proteins. A distinction is made, according to the amino acid residues to which the phosphate group is transferred, between, for example, protein serine/threonine kinases, protein hisitidine kinases, protein aspartate kinases or protein tyrosine kinases.

Protein kinases play a crucial part in regulating the activity of acceptor proteins (signal transduction cascade). Signals from outside the cell are picked up by cell surface receptors such as, for example, receptor tyrosine kinases (RTKs) (Ullrich et al. 1990, Cell, 61: 203-212; Fantl et al., 1993, Annu. Rev. Biochem., 62: 453-481). Autophosphorylation of RTKs takes place through the binding of "signal-emitting" molecules or so-called effectors or ligands (Weiss et al., 1997, Curr. Opin. Genet. Div., 7: 80-86). This autophosphorylation permits the RTKs to interact with other proteins, including so-called adapter proteins (Robertson et al., 2000, Trends Genet., 16: 268-271). These protein complexes are in turn able to activate other intracellular proteins, leading to a whole chain of protein interactions whereby the originally extracellular signal is transmitted from the cell surface into the cell nucleus (Treisman et al., 1996, Curr. Opin. Cell. Biol., 8: 205-215; Tan et al., 1999, Trends Genet., 15: 1456-149). The transmitted signal is thus able to influence gene expression, the cell cycle or other important cell functions.

The effectors of receptor tyrosine kinases include, for example, insulin and many growth factors such as, for example, the growth factors of the blood platelets (PDGF) or epidermal growth factors (EGF). Receptor tyrosine kinases play an important part inter alia in regulating the formation of new blood vessels (angiogenesis) or new lymphatic vessels (lymphangiogenesis). This entails endothelial cells from pre-existing vessels being stimulated to grow, to proliferate and to extend themselves in order to form new capillary vessels. Particular mention should be made in this connection of the cell surface receptors VEGFR (vascular endothelial growth factor receptor) and FGFR (fibroblast growth factor receptor) and, as effectors, corresponding growth factors of the VEGF family or FGF family (Korpelainen et al., 1998, Curr. Opin. Biol., 10: 159-164; Malonne et al., 1999, Clin. Exp. Metastasis, 17: 1-14). Further well-known examples of natural angiogenic effectors (ligands) are, inter alia, tumor necrosis factor (TNF-α), interleukin 8 or the so-called $Tie_2$ ligand (Malonne et al., 1999, Clin. Expl. Metastasis, 17: 1-14).

Uncontrolled stimulation of protein kinases may lead to pathological processes such as, for example, cancer (Porter et al., 1998, Oncogene, 17: 1343-1352). For example, a genetically modified receptor, i.e. a mutated receptor tyrosine kinase, which constitutively transmits, even in the absence of a suitable effector, signals to other proteins, may lead to the development of cancer. Such activation mutations of RTKs are linked to a large number of human diseases (Robertson et al., 2000, Trends Genet., 16: 268-271). Thus, for example, constitutively active FGF receptors are responsible for a large number of genetic diseases (Table 1). Incorrect regulation of angiogenesis plays an important part in the progress of a large number of diseases which are listed in Table 2 (Malonne et al., 1999, Clin. Exp. Metastasis, 17: 1-14). Thus, various studies have revealed in the case of cancers that tumors depend in a critical manner on an adequate blood supply. If angiogenesis can be inhibited, tumor growth can also be stopped or even reversed (Zetter et al., 1998, Annu. Rev. Med., 49: 407-424). Induction of lymphangiogenesis also plays an important part in cancers and filariasis (Skobe et al., 2000, Nature Med., 7: 192-198; Rao et al., 1996, J. Parasitol., 82: 550-556).

The protein kinase activity of receptor tyrosine kinases can in principle be regulated in various ways. Thus, for example, it is possible to employ antibodies which block the receptor kinase/ligand binding interaction (Brekken et al., 2000, Cancer Res., 60: 5117-5124; Klement et al., 2000, J. Clinic. Invest., Vol. 105, No. 8: 15-24). Alternatively, the use of soluble extracellular receptor sections for binding the appropriate ligand in an inactive complex (sequestration) is described by Aiello et al. (1995, Proc. Natl. Acad. Sci, Vol. 92: 10457-10461). Both the aforementioned antibodies and the soluble receptor portions have considerable disadvantages, however. Both are rapidly removed from the circulatory system. In addition, the molecules are very large in both cases, and their ability to penetrate tissue is very limited. Their preparation, especially that of the antibodies, for pharmaceutical application is very complicated and costly. Furthermore, they represent compounds which may induce an immune response, so that their biological efficacy is greatly reduced or entirely abolished.

A further possibility for regulating the activity of protein kinases is through inhibition by substrate-like compounds which compete for example with the natural substrate ATG or GTP for the substrate binding domain. Indolinones able to inhibit receptor tyrosine kinases (RTKs) have been described in this connection. Crystallographic studies on the specific RTK fibroblast growth factor receptor (FGFR) have shown that the oxindole portion of the indolinones interact with the same binding site as the adenine ring of the natural substrate ATP (Mohammadi, M. et al., Science, 276: 955-960). However, it chemical structure of the substituent on the C3 atom of the oxindole determines which RTK activity is inhibited. Some indolinones block the activity of a single RTK; other inolinones inhibit a wide range of RTKs.

In order to treat diseases in which the activity of protein kinases has become pathologically out of control, it is therefore of enormous medical relevance to provide compounds with which this uncontrolled activity of surface receptor protein kinases, advantageously receptor tyrosine kinases (RTKs), can be regulated, preferably blocked, in order thus to reduce or even suppress the progress of the disorders. Diseases in which the activity of protein kinases has become pathologically out of control may be, for example, types of cancer induced by uncontrolled cell proliferation and/or disordered apoptosis. Further possibilities are diseases such as, for example, filariasis or diseases induced by disordered angiogenesis and/or lymphangiogenesis processes (concerning this, see also Table 2). It is also desirable in this connection to provide compounds which, via the natural activity or pathologically altered (constitutive) activity of protein kinases, directly block angiogenesis and/or lymphangiogenesis, so that on the one hand the blood supply to the tumor is lessened or even stopped, leading to cessation of tumor growth or death of the pathological tissue, and on the other hand metastastis of tumor cells is prevented.

This object is achieved in an advantageous manner by the present invention.

The present invention relates to compounds which inhibit the activity of protein kinases which are involved in uncontrolled cell proliferation and/or disordered apoptosis of cells and/or angiogenesis and/or lymphangiogenesis and/or angiogenesis- and/or lymphangiogenesis-dependent disorders and/ or filariasis and represent a derivative, substituted on the C3 atom, of indolin-2-one, selected from the group of compounds of the general structural formula or salts of the compounds I)-III).

These compounds are also referred to in the course of the description as MAE87 (=structural formula I), MAE106 (=structural formula II), MAZ51 (=structural formula III). The present invention further relates to a compound called MAZ51-2 which, as a salt of the compound MAZ51, represents a more soluble variant of MAZ51 with otherwise comparable properties.

In an advantageous variant of the present invention, the compounds block the activity of receptor tyrosine kinases which are involved in angionesis and/or lymphangiogenesis. In a further variant, the compounds of the invention, singly or in combination thereof, inhibit the activity of receptor tyrosine kinases from the group of VEGFR-3 (vascular endothelial cell growth factor receptor), VEGFR-2, Tie2, EGFR (epidermal growth factor receptor), ErbB2, IGF1R and FGFR1 (fibroblast growth factor receptor). An advantageous variant of the invention includes compounds which block the activity of the cell surface receptor VEGFR-3.

For the purposes of the invention, the compounds inhibit not only the natural activity of protein kinases but also the activity of pathologically altered protein kinases, i.e. of protein kinases whose activity has become pathologically out of control. The protein kinases may be, for example, permanently (constitutively) stimulated. This may have been induced by altered properties in the interaction behavior with ligands (effectors), or other protein components or an altered autostimulation of the RTKs.

Pathologically altered protein kinase variants mean for the purposes of the present invention for example protein kinases which, owing to alterations at the nucleic acid and/or protein level, bring about uncontrolled cell proliferation and/or disordered apoptosis of cells and/or lead to disordered angiogenesis and/or lymphangiogenesis and to the diseases connected therewith (see Table 2) and/or are involved in the disease filariasis. Alterations at the nucleic acid level mean mutations according to the invention, for which for example deletions, insertions or exchanges of one or more nucleotides are to be understood. Alterations at the protein level mean deletions, insertions or exchanges of one or more amino acids.

The principle of action of the compounds of the invention is based on their simulation of the natural substrate of the protein kinases, for example ATP. This means that they act as ATP analogs as it were. This involves them binding with their oxindole portion to the same domain of the protein kinases to which the adenine ring of ATP naturally binds. The compounds of the invention and the natural substrate thus compete for the substrate binding site, i.e. the compounds of the invention displace the ATP from the substrate binding site. For this reason, the protein kinases are unable to catalyze any transfer of a phosphate group to a target molecule, and are thus no longer able to exercise their intended function as kinase. The compounds of the invention are thus by reason of their structure able not only generally to inhibit the activity of protein kinases but also to treat human disorders induced by mutated (constitutively) active RTKs. It is conceivable in this connection to use each of the compounds singly, but also combinations thereof.

The compounds of the invention have the advantages that they are small molecules exhibiting very good cell and tissue penetrance. They are also very suitable for administration to the patient, preferably orally. In addition, preparation of the compounds for pharmaceutical use is simple and cost-effective even on the industrial scale. It is moreover particularly advantageous that these compounds do not induce an immune response.

The present invention also relates to compositions comprising at least one compound of the invention of the aforementioned type for the treatment of disorders in the development, progress, alleviation and/or cure of which naturally occurring and/or pathologically altered protein kinases are involved. This includes according to the invention compositions for inhibiting uncontrolled proliferation and/or inducing apoptosis of cells and/or for inhibiting angiogenesis and/or lymphangiogenesis comprising at least one compound of the aforementioned type. The compositions of the invention comprising at least one compound of the invention are also suitable for the treatment of angiogenesis- and/or lymphangiogenesis-dependent disorders (as listed for example in Table 2) and/or filriasis. The aforementioned compositions are further distinguished by comprising at least one compound of the type according to the invention in a concentration of about 1-20, preferably of about 2-15, particularly preferably about 3-10 and especially of about 4-8, mg/kg of the subject's body weight. Also conceivable are combinations of the compounds of the invention in freely combinable concentration proportions of the ranges mentioned.

The invention also includes compositions comprising at least one compound of the aforementioned type for regulating the biological function of proteins which themselves are controlled in terms of their activity by protein kinases which in turn are inhibited by the compounds of the invention (signal transduction).-

It is additionally possible for the compositions of the invention to comprise additional substances which are necessary or suitable for better processing or administration to the patient. These substances, just like the processes for producing the compositions of the invention, are routine laboratory practice and are therefore not explained in detail here.

The present invention relates to the use of the compounds of the aforementioned type for producing compositions for inhibiting the uncontrolled proliferation and/or inducing the apoptosis of cells and/or for inhibiting angiogenesis and/or lymphangiogenesis. Likewise included is the use of the compounds of the invention for the treatment of angiogenesis- and/or lymphangiogenesis-dependent disorders (Table 2) and/or filariasis.

The following examples serve to illustrate the present invention but do not have a limiting effect on the invention:

1) Structure and Synthesis of MAE87, MAE106 and MAZ51

General Method:

10 mmol of oxoindole, 10 mmol of aldehyde and a few drops of piperidine are dissolved in 40 ml of ethanol. The reaction mixture is stirred at 90° C. for 5 hours. The desired product (E/Z mixture) precipitates during the reaction or after cooling to room temperature. The precipitate is filtered off, washed with ethanol and dried in vacuo.

The NMR spectra were recorded on a Bruker DRX500 spectrometer. The chemical shifts are stated in ppm (parts per million). The residual proton signal of the solvents serves as internal standard. High-resolution mass spectra were recorded using a Finnigan MAT MS 70 mass spectrometer. The melting points are uncorrected.

1a) 3-(2,4-Dihydroxybenzylidene)-1,3-dihydroindol-2-one (MAE87)

A mixture of 1.33 g of indole-2-one (10 mmol), 1.38 g of 2,4-dihydroxybenzaldehyde (10 mmol) and 3 drops of piperidine are refluxed in 40 ml of ethanol for 5 hours. The desired product precipitates as a yellow solid during the reaction. After cooling to room temperature, the product is filtered off, washed with ethanol and dried in vacuo. Yield 1.28 g (51%).

Melting point: 250° C. decomposition $^1$H-NMR (500 MHz, DMSO-$d_6$):

δ [ppm]: 6.38 (dd, J=2 Hz, J=8.5 Hz, 1H); 6.44 (d, J=2 Hz, 1H); 6.85 (m, 2H); 7.17 (t, J=7.5 Hz, 1H); 7.55 (d, J=8.3 Hz, 1H); 7.63 (d, J=7.6 Hz, 1H); 7.7 (s, 1H); 10.2 (br, 2H); 10.45 (s, 1H)

$^{13}$C-NMR (125 MHz, DMSO-$d_6$):

δ [ppm]: 102.9; 107.4; 110.2; 113.1; 121.3; 122.2; 122.3; 123.5; 129.2; 131.2; 133.4; 142.5; 159.2; 161.7; 169.7

HR-MS: $C_{15}H_{11}NO_3$: calc.: m/z=253.0739 found: m/z 253.0744

1b) 3-(3-Fluoro-4-methoxybenzylidene)-1,3-dihydroindole-2-one (MAE106)

A mixture of 1.33 g of indole-2-one (10 mmol), 1.54 g of 3-fluoro-4-methoxybenzaldehyde (10 mmol) and 3 drops of piperidine are refluxed in 40 ml of ethanol for 5 hours. The desired product precipitates as a yellow crystalline solid during the reaction. After cooling to room temperature, the product is filtered off, washed with ethanol and dried in vacuo. Yield 2.2 g (82%).

Melting point: 220° C.

$^1$H-NMR (500 MHz, DMSO-$d_6$ E/Z isomers:

δ [ppm]: 3.92 (s, 3H); 6.83 (d, J=7.2 Hz, 0.7H); 6.87 (m, 0.7H); 6.98 (t, J=7.6 Hz, 0.7H); 7.18-7.32 (m, 2H); 7.54 (s, 0.3H); 7.6 (m, 1H); 7.65 (d, J=7.6 Hz, 0.6H); 7.74 (s, 0.7H); 8.0 (d, J=8.3 Hz, 0.7H); 8.80 (dd, J=2 Hz, J=13 Hz, 0.6H); 10.65 (br, 1H)

$^{13}$C-NMR (125 MHz, DMSO-$d_6$):

δ [ppm]: 109.8; 110.6; 113.6; 114.3; 117.4; 117.6; 118.9; 119.0; 119.9; 121.3; 121.5; 121.6; 122.6; 125.5; 125.7; 121.1; 127.2; 127.5; 127.6; 127.7; 127.8; 129.1; 130.5; 121.1; 135.1; 136.2; 140.9; 143.3; 148.7; 148.8; 149.5; 149.6; 150.0; 150.6; 151.9; 152.5; 167.8; 169.2

HR-MS: $C_{16}H_{12}NO_2F$: calc.: m/z=298.9946 found: m/z 298.9954

1c) 3-(4-Dimethylaminonaphthalen-1-ylmethylene)-1,3-dihydroindol-2-one (MAZ51)

A mixture of 1.33 g of indole-2-one (10 mmol), 1.99 g of 4-dimethylamino-1-naphthaldehyde (10 mmol) and 3 drops of piperidine are refluxed in 40 ml of ethanol for 5 hours. The desired product precipitates as an orange solid during the reaction. After cooling to room temperature, the product is filtered off, washed with ethanol and dried in vacuo. Yield 2.67 g (85%).

$^1$H-NMR (500 MHz, DMSO-$d_6$):

δ [ppm]: 2.90 (s, 6H; $(CH_3)_2$) 6.74 (dt, J=1 Hz, J=7.5 Hz, 1H); 6.87 (d, J=7.5 Hz, 1H); 7.15 (m, 2H); 7.24 (d, J=8 Hz, 1H); 7.59 (m, 2H); 7.83 (d, J=8 Hz, 1H); 7.93 (m, 1H); 8.06 (s, 1H); 8.23 (m, 1H); 10.64 (br, 1H, —NH).

$^{13}$C-NMR (125 MHz, DMSO-$d_6$):

δ [ppm]: 45.1; 110.4; 113.4; 121.4; 121.7; 122.7; 125.2; 125.3; 125.4; 126; 127.4; 128.1; 128.2; 128.3; 130.2; 132.8; 134.1; 143.2; 153.1; 169

HR-MS: $C_{21}H_{18}N_2O$: calc.: m/z=314.1419 found: m/z 314.1419

Melting point: 250° C. decomposition

2) MAE87, MAE106 and MAZ51 Inhibit a Large Number of Receptor Tyrosine Kinases in the In Vitro Tyrosine Kinase Assay.

| Inhibitor | | Kinase | | | | | | |
|---|---|---|---|---|---|---|---|---|
| Name | Conc. | VEGFR-3 | VEGFR-2 | Tie2 | EGFR | ErbB2 | IGF1R | FGFR1 |
| MAE87 | 1 µg/ml | −9 | −46 | +1 | −70 | −45 | −63 | −50 |
|  | 10 µg/ml | −74 | −77 | −65 | −86 | −84 | −94 | −94 |
| MAE106 | 1 µg/ml | +1 | +21 | −5 | −5 | +4 | −10 | +5 |
|  | 10 µg/ml | −57 | −58 | −28 | −64 | −41 | −71 | −1 |
| MAZ51 | 1 µg/ml | −4 | −8 | −7 | −25 | −11 | −10 | +1 |
|  | 10 µg/ml | −35 | −74 | −27 | −58 | −39 | −68 | −5 |

The inhibition of various receptor tyrosine kinases in vitro by MAE87, MAE106 and MAZ51 was investigated. The inhibitors were investigated in 2 different concentrations (1 µg/ml and 10 µg/ml). The inhibition is stated in %. "+"=stimulation of kinase activity relative to the control, "−"=inhibition of kinase activity relative to the control.

The activity of the RTK inhibitors were determined with the aid of an ELISA. In this assay, the corresponding kinases were employed as recombinant GST fusion proteins (glutathione S-transferase). Synthetic polyGlu, Tyr 4:1 is used as acceptor. The ability of different concentrations of the test substances to inhibit the RTK-mediated phosphorylation of the abovementioned acceptor was assessed. All the tests were carried out in duplicate.

ELISA plates were coated with 0.2 mg/ml of polyGlu, Tyr 4:1 in 100 mM bicarbonate buffer (pH 9.6) overnight. This solution was removed and the microtiter plates were washed twice with TBS buffer (10 mM Tris-HCl, pH 8.1, 100 mM NaCl) and then blocked with 5% BSA/TBS for 30 min. 50 µl of test substance (2 or 20 µg/ml in 10% DMSO), 25 µl of GST kinase in 4× kinase buffer (200 mM HEPES, 100 mM NaCl, 80 µM $Na_3VO_4$ and 0.04% BSA) were introduced. The reaction was started by adding 25 µl of 160 µM ATP (in 40 mM $MnCl_2$) as substrate of the kinases. The final concentrations of the test compounds is thus 1 or 10 µg/ml in 5% DMSO. The GST fusion proteins were employed in the following concentrations. VEGFR-2 50 NG/well, VEGFR-3 300 ng/well, Tie2 300 ng/well, EGFR 50 ng/well, ErbB2 200 ng/well, IGF-1R 50 ng/well, FGFR1 200 ng/well. The reaction mixture was incubated at 30° C. for 90 min. The kinase reaction was stopped by adding 50 µl of 30 mM EDTA/well. The microtiter plates were washed twice with 0.05% Tween20/TBS. Anti-phosphotyrosine antibody (1:500) was added in 0.05% Tween20/TBS (with 0.5% BSA, 0.025% skimmed milk powder and 100 µM $Na_3VO_4$) and incubated at 37° C. for 1 h. The microtiter plates were washed three times with 0.05% Tween20/TBS. The HRP-conjugated detection autibody (1:1000) was added in 0.05% Tween20/TBS (with 0.5% BSA, 0.025% skimmed milk powder and 100 µM $Na_3VO_4$) and incubated at 37° C. for 1 h. The microtiter plates were washed three times with 0.05% Tween20/TBS. ABTS (2,2'-azino-di-(3-ethylbenz-thiazoline-6-sulfonate)) substrate (Roche Diagnostics GmbH, Mannheim) was added. The OD was determined at 405 nm using an ELISA reader.

3) MAE87, MAE106 and MAZ51 Inhibit the Ligand-Induced Autophosphorylation of the RTKs VEGFR-2 and VEGFR-3

VEGFR-2- and VEGFR-3-expressing PAE cells (pig aorta endothel cells) were incubated with 0.5 µM, 5 µM or 50 µM of the appropriate test compound. The cells were then stimulated with VEGF (VEGFR-2) or VEGF-C (VEGFR-3) or without growth factor as negative control. The cells were harvested after 15 min and immunoprecipitated with VEGFR-2 or VEGFR-3. The immunoprecipitates were blotted after electrophoresis and investigated with anti-phosphotyrosine antibody. The blots were detached and investigated with VEGFR-2 or VEGFR-3 antibody to check the loading. At 5 µM, MAZ51 selectively inhibits VEGFR-3.

PAE/VEGFR-2 or PAE/VEGFR-3 were seeded in 15 cm tissue culture tissues and cultivated to 50% confluence. The cells were then starved in serum-free medium (with 0.2% BSA) for 16-24 h (PAE/VEGFR-3) or 72 h (PAE/VEGFR-3). After preincubation with 5 ml of 1 mM serum-free medium (1 mM $Na_3VO_4$) and various inhibitor concentrations for 30-60 min, the cells were stimulated at 37° C. for 5 min (VEGFR-3) or 8 min (VEGFR-2). The cells were then rapidly washed twice with ice-cold PBS (with 1 mM $Na_3VO_4$) and lysed with ice-cold modified RIPA buffer (30 mM Tris-HCl, pH 7.4, 150 mM NaCl, 1 mM EDTA, 0.5% (v/v) Triton X100, 0.5% (w/v) sodium deoxycholate, 10 mM NaF) freshly prepared with 1 mM PMSF, 0.1 U/ml aprotinin, 10 ng/ml leupeptin and 5 mM $Na_3VO_4$. The cells were harvested from the plate with the aid of a rubber policeman and collected in centrifuge tubes on ice. The lysates were solubilized by forcing through a syringe with a 25 G needle, and were centrifuged at 4° C./13 000 rpm for 15 min to remove insoluble constituents.

The clear lysates were incubated with 4 µg of anti-VEGFR-2 (C-1158, Santa Cruz) or anti-VEGFR-2 antibody (M20, Santa Cruz) at 4° C. overnight.

The receptor-antibody complex was precipitated by adding 30 µl of protein A-Sepharose (Amersham)/tube and incubating at 4° C. for a further 2 hours.

The Sepharose were then centrifuged at 4° C. for 1 min and washed three times with cold washing buffer (30 mM Tris-HCl, pH 7.4, 150 mM NaCl, 1 mM EDTA, 0.5% (v/v) Triton X100, 0.5% (w/v) sodium deoxycholate, 10 mM NaF) freshly prepared with 1 mM PMSF, 0.1 U/ml aprotinin, 10 ng/ml leupeptin and 5 mM $Na_3VO_4$. The remainder of the washing buffer was removed by aspiration through a syringe provided with a 27 G needle. The Sepharose beads were resuspended in 50 µl of SDS loading buffer, boiled and loaded onto a 6% agarose gel. After the electrophoretic fractionation, the proteins were fixed on an appropriate membrane by Western blotting. The blots were investigated first with the aid of an anti-phosphotyrosine antibody (RC20:HRPO, Becton Dickinson) and then the first antibody was removed again in order to investigate the blot for the protein loading with specific anti-receptor antibodies. The first antibody was stripped off by shaking the membranes with stripping buffer (62.5 mM Tris, pH 6.8, 2% SDS, 0.75% 2-mercaptoethanol) at 55° C.

for 20 min. The membranes were then washed twice with TBST for 2 min each time and blocked and incubated as usual.

Figure 1:
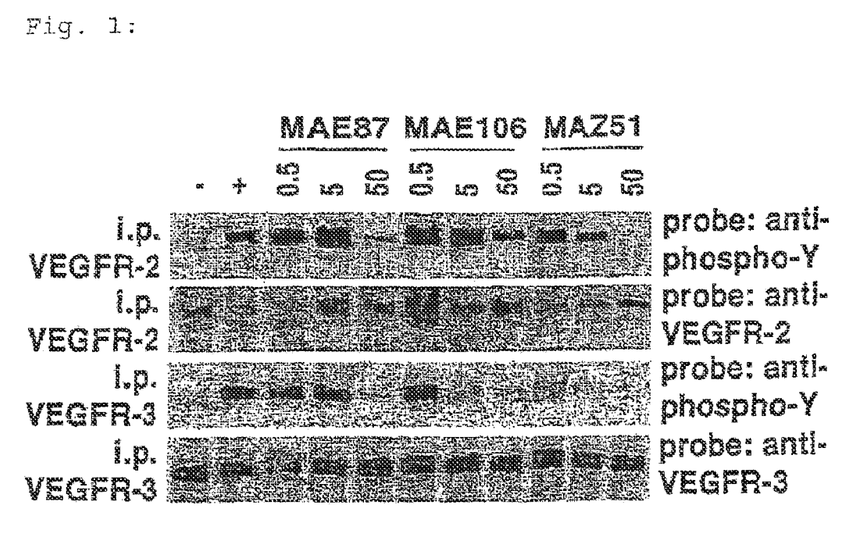
FIG. 1: Western blot of immunoprecipitations (i.p.) of VEGFR-2 and VEGFR-3 from PAE cells treated with MAE87, MAE106 and MAZ51. (–) represents the control (unstimulated cells); (+) are growth factor-stimulated cells treated without or with 0.5 µM, 5 µM or 50 µM of the appropriately indicated inhibitor (MAE87, MAE106 or MAZ51). The antibody probes (probe) employed for the immunoprecipitation is either anti-phosphotyrosine antibody (anti-phospho-Y), anti-VEGFR-2-antibody (anti-VEGFR-2) or anti-VEGFR-3-antibody (anti-VEGFR-3).

The result is depicted in FIG. 1.

4) MAE87, MAE106 and MAZ51 Inhibit Endothelial Cell Proliferation

Human umbilical vein endothelial cells (HUVEC) underwent serum-starved cultivation for 24 h. The cells were then preincubated with the appropriate compounds for 2 h and subsequently cultivated in the presence of the inhibitors with VEGF (MAE87) or bFGF (MAE106, MAZ51) for a further 24 h. The cells were then incubated with $^3$H-thymidine. The amount of radioactivity incorporated into the cellular DNA was measured. All the experiments were carried out in triplicate.

Figure 2:
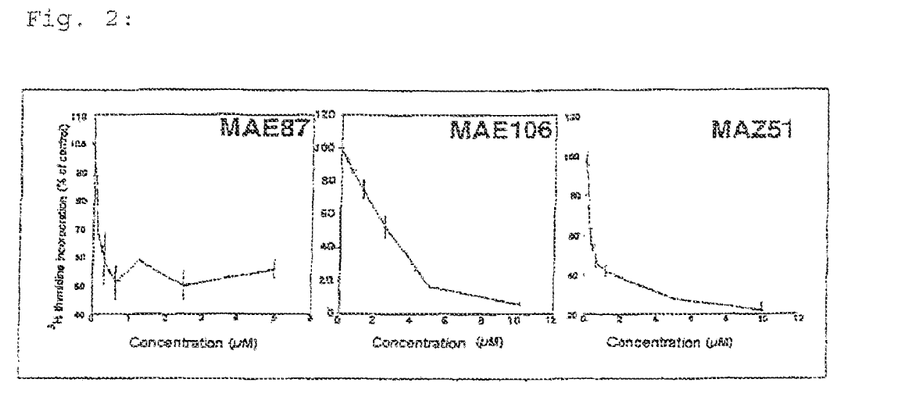
FIG. 2: Measurement of the ($^3$H)-thymidine incorporation into human endothelial cells (HUVEC) as a function of the concentration of inhibitors employed (MAE87, MAE106 and MAZ51). The inhibition of cell proliferation by MAE87, MAE106 and MAZ51 is dose-dependent in this case.

HUVE cells were seeded in 100 µl/well ($10^5$ cells/ml) in 96-well culture plates and left to rest overnight. The cells were then starved with 50 µl of serum-free medium/well for 24 h. Subsequently, 50 µl of various concentrations of the test substances in serum-free medium (contains 2% DMSO) were added and incubated at 37° C. for 2 h. The medium containing the test compounds was removed and replaced by 50 µl of fresh medium with bFGF (12.5 ng/ml) or VEGF (100 ng/ml). Fresh dilutions of the doubly concentrated test substances in serum-free medium with 2% DMSO were added to the cells in 50 µl/well. The final concentration of DMSO was always 1%. After 24 h, $^3$H-thymidine (1 µCi/well) was added, and the cells were incubated for a further 4-6 h. To analyze the incorporated radioactivity, the cells were trypsinized for 30 min and harvested with the aid of a harvester 96 cell (Tomtec) and fixed on a glass fiber membrane filter. The immobilized radioactivity was quantified with the aid of a MicroBeta TriLux liquid scintillation luminescence counter. The result is depicted in FIG. 2.

5) MAE87, MAE106 and MAZ51 Inhibit Angiogenesis in the CAM Assay

Figure 3:
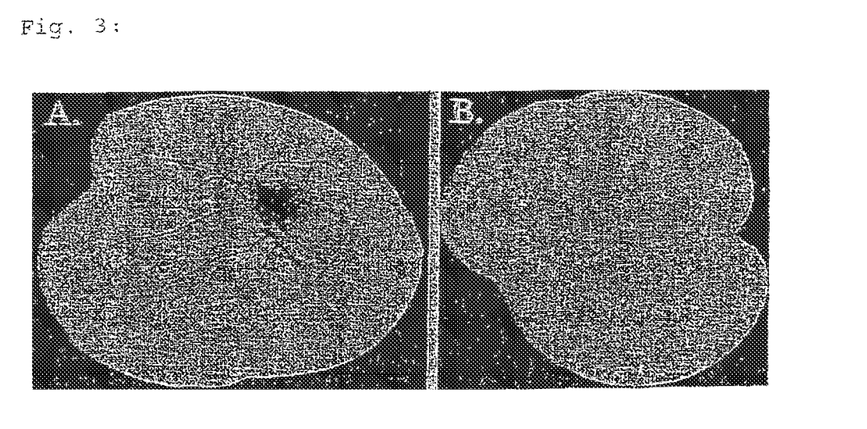
FIG. 3: Inhibition of angiogenesis in a chorioallantoic membrane (CAM). A: sham-treated cells (control). B: Mae106-treated cells of the CAM.

The chorioallantoic membrane (CAM) assay was carried out as described (Wernert et al.) with chick embryos 5 days after fertilization. Methylcellulose disks (diameter 2 mm) with 100 µg of inhibitor were applied to the CAMs. Evaluation took place on day 7. Representative results for MAE106 are shown in FIG. 3. A. negative control B. MAE 106-treated egg. The highly branched network of blood vessels shown by the negative control is highly underdeveloped in the MAE 106-treated egg.

6) MAE87, MAE106 and MAZ51 Inhibit the Proliferation of Tumor Cells

Cells of the rat tumor cell line (Nestl et al., 2001, Cancer Research 61: 1569-1577) were cultivated in the presence of 1% DMSO (solvent control), 2.5 µM or 10 µM of the indolinone for 24 h. Tritiated thymidine was added to the medium during the last 4-6 h of incubation. The cells were harvested and the amount of radioactivity incorporated into the DNA was quantified.

Figure 4:
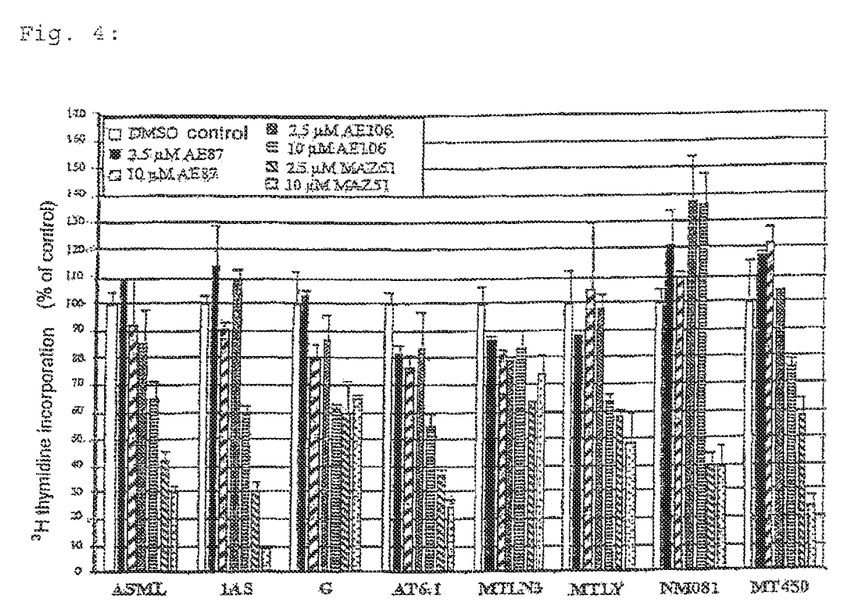
FIG. 4: Measurement of the ($^3$H)-thymidine incorporation (in %) into rat tumor cell lines (ASML, 1AS, G, AT6.1, MTLN3, MTLY, NM081 and MT450) as a function of the concentration of inhibitors employed. The inhibition of cell proliferation by MAE87, MAE106 and MAZ51 is dose-dependent.

The data are stated in percent relative to the proliferation of the cells treated only with DMSO (% relative to control; see FIG. 4)). MAZ51 had the greatest inhibitory effect.

Figure 5:
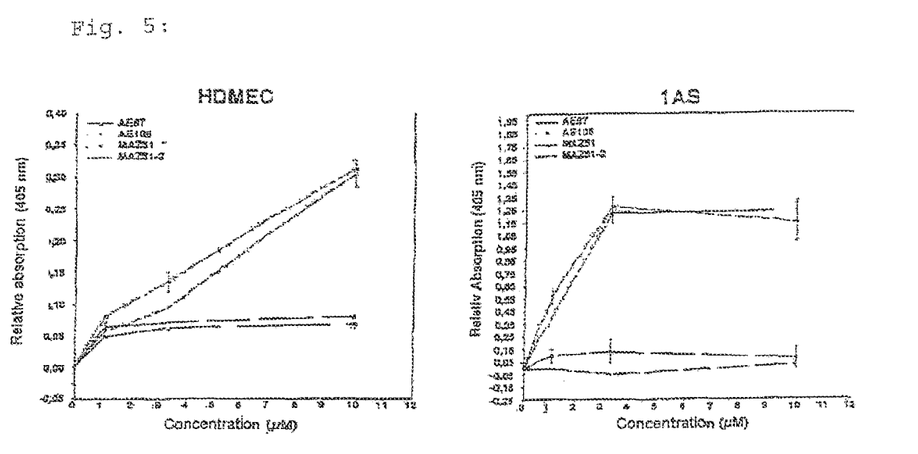
FIG. 5: Nucleosome ELISA test (Cell Death Detection ELISA). The extent of dead cells of the respective cell line is depicted (as relative absorption at 405 nm) in relation to the use of the inhibitors MAE87, MAE106 and MAZ51 and MAZ51-2. MAZ51 is the most effective at inducing cell death in human endothelial cells (HDMEC) and the rat pancreatic cell line 1AS.

7) MAE87, MAE106 and MAZ51 Induced Apoptosis in Endothelial Cells and Tumor Cells Human endothelial cells (HDMEC) and rat pancreatic tumor cells (1AS) were resuspended ($10^5$ cells/ml). 50 µl of cell suspension were seeded in 96-well cell culture plates and incubated at 37° C. for 24 h. The cells were then incubated with the stated concentrations of the various inhibitors for a further 24 h. The pro-apoptotic effect of the compounds was determined using the Cell Death Detection ELISA$^{plus}$ kit (Roche Diagnostics GmbH, Mannheim) in accordance with the manufacturer's statements. The kit contains a photometric enzyme immunoassay for qualitative and quantitative in vitro determination of cytoplasmic histone-associated DNA fragments (mono- and oligo-nucleosomes) released through active cell death (apoptosis). The proportion of induced apoptosis can be quantified by determining the optical density at 405 nm. The measurements relative to the untreated cells are plotted against the inhibitor concentration. The results in FIG. 5 show that MAZ51 is a potent activator of apoptosis both in endothelial cells and tumor cells.

Figure 6:
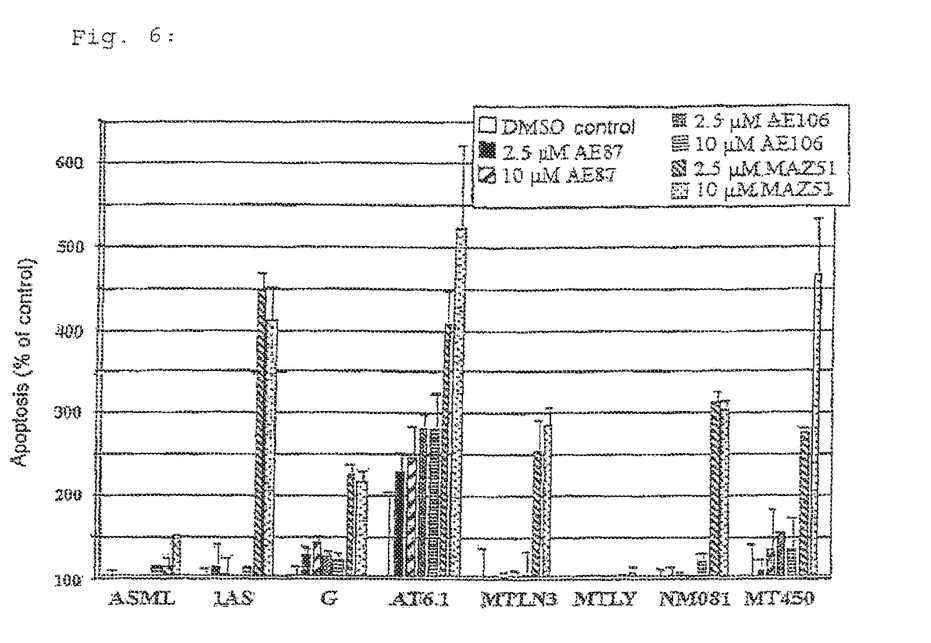
FIG. 6: Nucleosome ELISA test (Cell Death Detection ELISA). The extent of dead cells of the respective rat tumor cell line is depicted (apoptosis in %) in relation to the use of the inhibitors MAE87, MAE106 and MAZ51. MAE87, MAE106 and MAZ51 induce cell death in a number of rat carcinoma cell lines.

Cells of the rat tumor cell line (Nestl et al., 2001, Cancer Research 61: 1569-1577) were cultivated in the presence of 1% DMSO (solvent control), 2.5 µM or 10 µM of the indolinone for 24 h. Apoptosis was quantified with the aid of anti-DNA peroxidase antibody. The amount of dye produced in the chromogenic reaction catalyzed by the peroxidase was measured by photometry at 405 nm and correlated with the amount of apoptosis-associated cytoplasmic mono- and oligonucleosomes. The data are stated in % apoptosis relative to the cells of the solvent control (% relative to control) (FIG. 6). MAZ51 is the most potent apoptosis inducer.

8) MAZ51 Inhibits the Growth of 1AS and MT450 Rat Carcinomas In Vivo.

Figure 7:
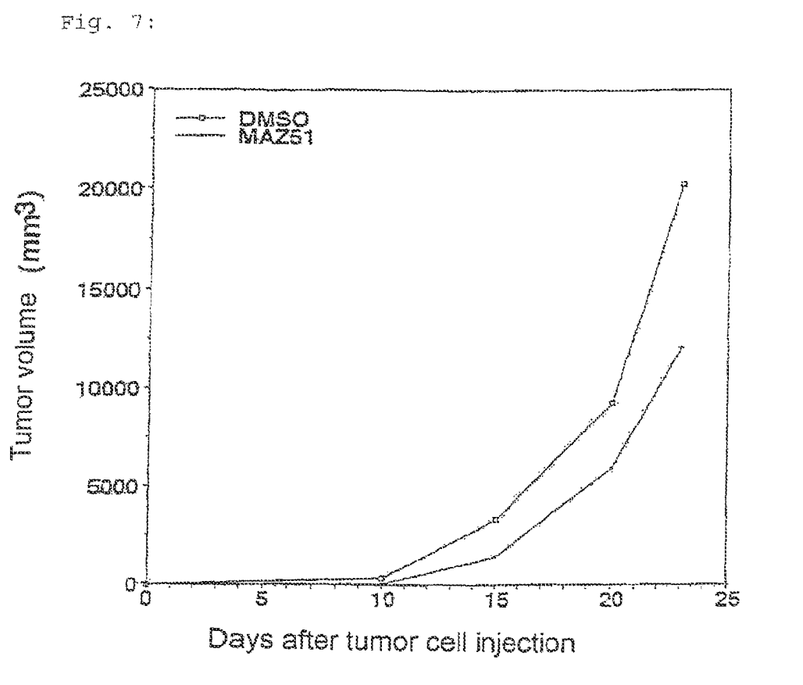
FIG. 7: Depiction of the tumor volume as a function of the number of days after tumor cell injection depending on the treatment of the 1AS tumor cells with MAZ51. The investigated rats show that tumor growth is inhibited in vivo after treatment of 1AS tumor cells with MAZ51.

1AS cells ($5\times10^5$) were injected subcutaneously into 2 groups of BDX rats (8 rats per group). One group was subsequently injected with 100 µl of DMSO/animal per day up to the end of the experiment. The other group was injected with 100 µl of MAZ51 (10 mg/ml in DMSO)/animal, equivalent to 4-5 mg/kg, each day. The tumor volume was measured normally measured regularly after the injection of the tumor cells. As can be seen from FIG. 7, the growth of AS1 tumors in vivo is considerably inhibited through treatment with MAZ51.

Figure 8:
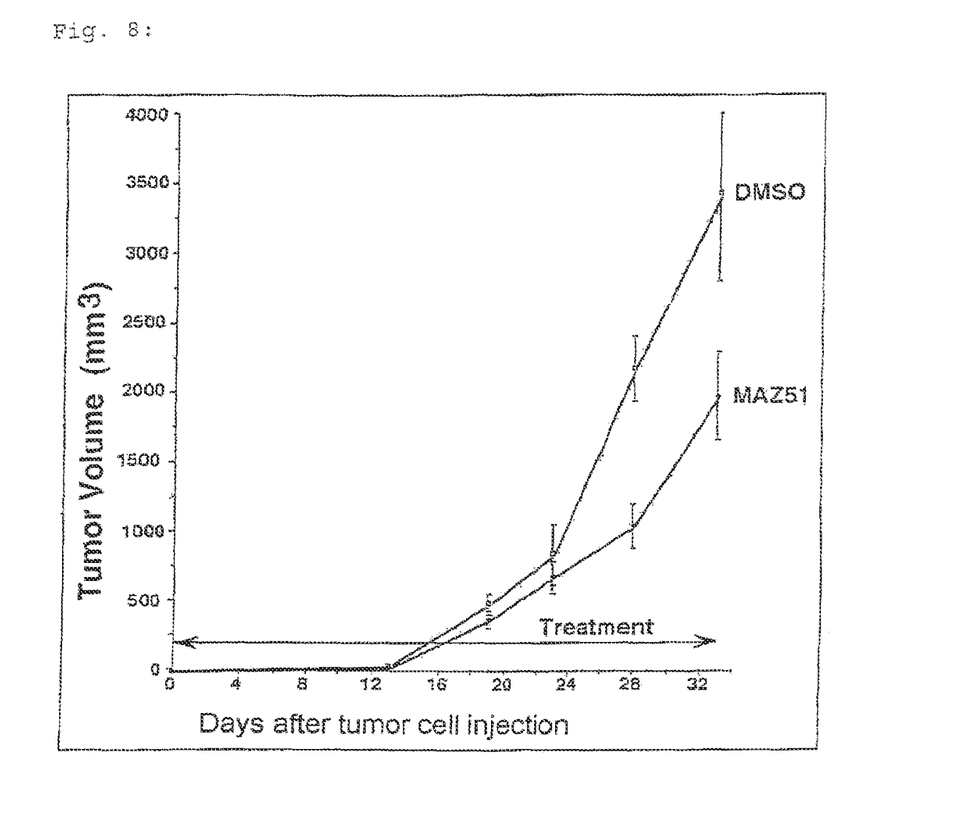
FIG. 8: Depiction of the tumor volume as a function of the number of days after tumor cell injection depending on treatment of the MT450 tumor cells with MAZ51 and a DMSO solution (negative control). The investigated rats show that tumor growth of MT450 tumor cells is inhibited in vivo after treatment with MAZ51. +/−SE means the standard deviation of the tumor volume from the average of 8 investigated rats per batch.
Figure 9:
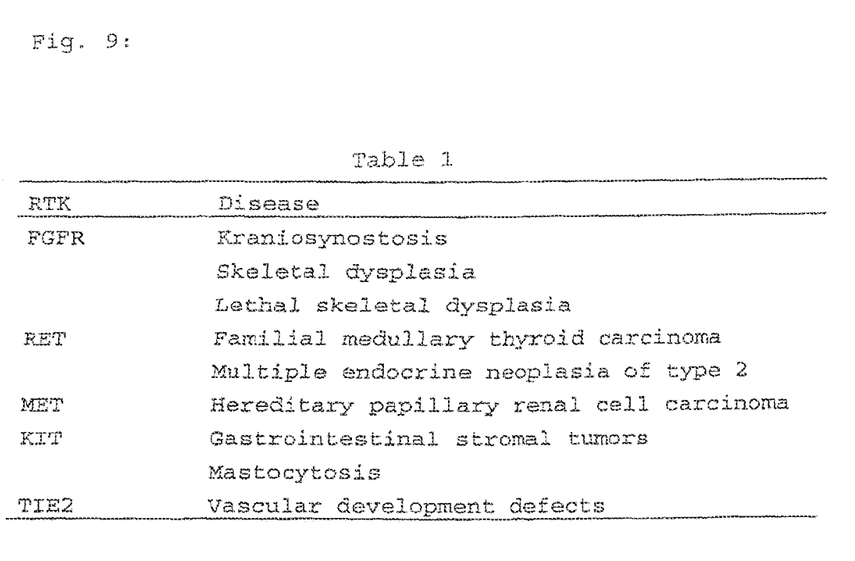
FIG. 9 Table 1 containing a survey of activation mutations of various receptor tyrosine kinases and the diseases induced thereby.
Figure 10:
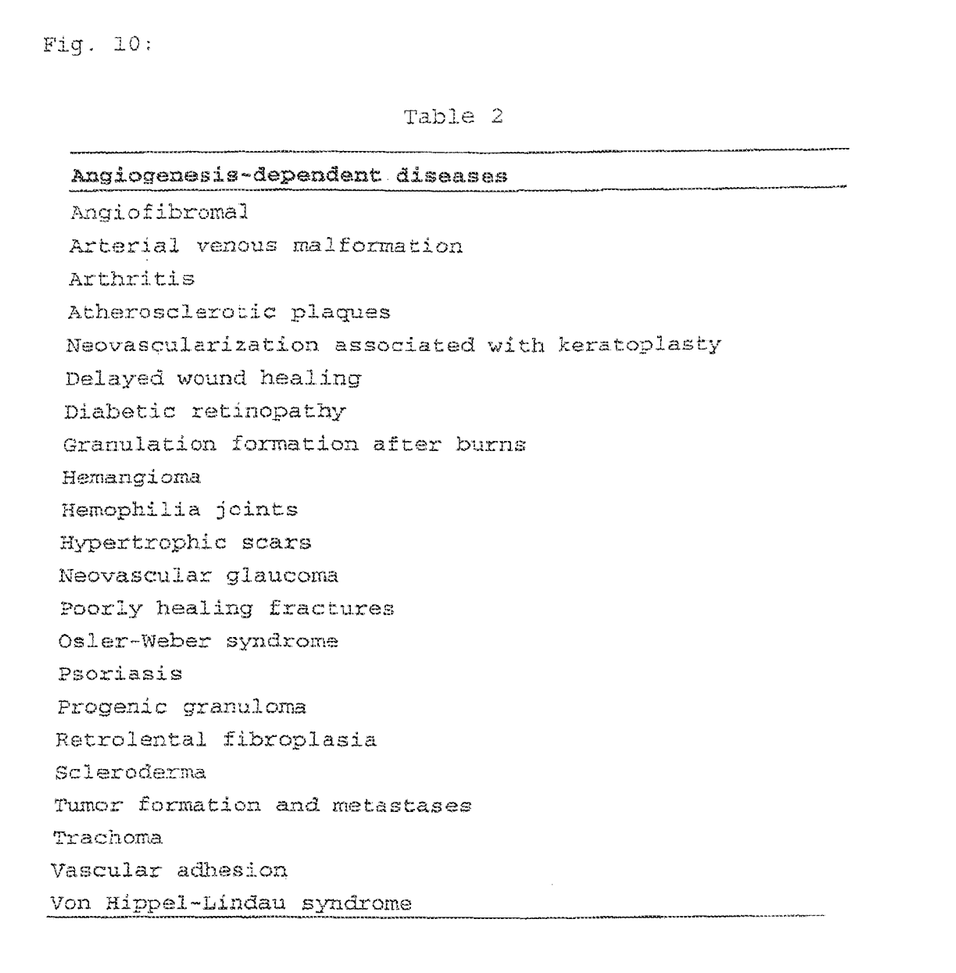
FIG. 10 Table 2 containing a survey of antiogenesis-dependent diseases.

MT450 rat mammary carcinoma cells were injected subcutaneously into Wistar Furth rats. Treatment with the active substance MAZ51 at 8 mg/kg/day in 100% DMSO or solvent control (100% DMSO) was started the day after injection of the tumor cells. MAZ51 or only solvent was injected intraperitoneally each day. Each test group comprised 8 animals. The tumors were measured every 4-5 days. The average tumor volumes are indicated in FIG. 8.

The invention claimed is:

1. A method for inhibiting the activity of cell surface receptor VEGFR-3, comprising the steps of: administering to a subject a composition comprising a compound of the general structural formula or salts of the compound that inhibits activity of the cell surface receptor VEGFR-3; and administering a therapeutically effective amount of the composition to a subject to inhibit activity of the cell surface receptor VEGFR-3.

* * * * *